United States Patent [19]

McPhail et al.

[11] Patent Number: 4,550,186
[45] Date of Patent: Oct. 29, 1985

[54] BINUCLEAR COPPER (II) CARBOXYLATES FORMED FROM AMINE-CARBOXYBORANES

[75] Inventors: Andrew T. McPhail, Durham; Bernard F. Spielvogel, Raleigh; Iris H. Hall, Chapel Hill, all of N.C.

[73] Assignee: Duke University, Durham, N.C.

[21] Appl. No.: 512,729

[22] Filed: Jul. 11, 1983

[51] Int. Cl.$^4$ ............................................. C07F 1/08
[52] U.S. Cl. ...................... 556/8; 423/284; 546/2; 546/3; 514/499
[58] Field of Search ............... 260/438.1; 546/2, 13; 423/284

[56] References Cited

U.S. PATENT DOCUMENTS

| | | | |
|---|---|---|---|
| 3,298,798 | 1/1967 | Lirngiebl et al. | 423/284 X |
| 3,989,732 | 11/1976 | Gysling | 260/438.1 |
| 4,209,510 | 6/1980 | Spielvogel et al. | 423/284 X |
| 4,312,989 | 1/1982 | Spielvogel et al. | 546/13 |
| 4,394,321 | 7/1983 | Cone | 260/438.1 X |
| 4,416,824 | 11/1983 | Reimer et al. | 260/439 R |

OTHER PUBLICATIONS

Chemical Abstracts 100, 132207r, (1984).
Chemical Abstracts 93, 230746x, (1980).
Chemical Abstracts 94, 167687g, (1981).
Chemical Abstracts 101, 65816u, (1984).

Primary Examiner—Helen M. S. Sneed
Attorney, Agent, or Firm—Oblon, Fisher, Spivak, McClelland & Maier

[57] ABSTRACT

A compound of the formula

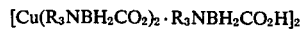

$[Cu(R_3NBH_2CO_2)_2 \cdot R_3NBH_2CO_2H]_2$ wherein each R independently represents H, $C_1$–$C_{10}$ alkyl, or phenyl and L represents a non-toxic Lewis base capable of forming a coordinate bond with the copper with the provisos that any two or three R attached to the same nitrogen may represent a $C_4$–$C_5$ alkylene group containing up to 2 non-cumulative double bonds optionally having 1 or 2 carbons replaced by oxygen or nitrogen, that any 3 R attached to the same nitrogen when taken together with the nitrogen may represent a 6-membered aromatic ring containing 1, 2 or 3 nitrogen atoms, and that any R containing a carbon atom may be substituted with a hydroxyl, ether, ester, carboxyl, or amino functional group is disclosed along with methods of making these compounds and methods of using these compounds as antihyperlipidemic agents and antineoplastic agents.

8 Claims, 3 Drawing Figures

BINUCLEAR COPPER (II) CARBOXYLATES FORMED FROM AMINE-CARBOXYBORANES

The investigations leading to the present invention were supported in part by Grant 1 RO1 HL25680 from the National Institutes of Health and the U.S. Army Grant.

BACKGROUND OF THE INVENTION

1. Field of the Invention

The present invention relates to boron-containing analogs of amino acids and to copper-containing pharmaceutical compositions.

2. Description of the Prior Art

Amine-carboxyboranes (boron analogs of α-amino acids), amine-cyanoboranes, and related derivatives have received considerable attention recently because of their anti-inflammatory, anti-arthritic, anti-tumor and anti-hyperlipidemic activity. See, for example, Hall et al, *J. Pharm. Sci.*, 68:685 (1979); Hall et al, *J. Pharm. Sci.*, 69:1025 (1980); and Hall et al, *J. Pharm. Sci.*, 70:339 (1981). However, because of the relative newness of this area of research, there continues to be significant interest in new amine-carboxyborane compounds, particularly those having increased pharmacological activities.

SUMMARY OF THE INVENTION

It is an object of the present invention to provide amine-carboxyborane compounds having increased pharmacological activity.

This and other objects of the invention as will hereinafter become more readily apparent have been accomplished by providing a compound of the formula $$[Cu(R_3NBH_2CO_2)_2 \cdot L]_2$$

wherein each R independently represents H, $C_1-C_{10}$ alkyl, or phenyl, and L represents a non-toxic Lewis base capable of forming a coordinate bond with said Cu with the provisos that any two or three R attached to the same nitrogen may represent a $C_4-C_5$ alkylene group containing up to 2 non-cumulative double bonds optionally having 1 or 2 carbons replaced by oxygen or nitrogen, that any 3 R attached to the same nitrogen when taken together with the nitrogen may represent a 6-membered aromatic ring containing 1, 2 or 3 nitrogen atoms, and that any R containing a carbon atom may be substituted with a hydroxyl, ether, ester, carboxyl, or amino functional group.

Compounds of the invention have been demonstrated to be particularly useful as antihyperlipidemic agents in that they can be used at dosages lower than previously available for similar compounds. These compounds have also been demonstrated to have antineoplastic activity. Accordingly, the present invention also encompasses methods of using these compounds as antihyperlipidemic and antineoplastic agents.

BRIEF DESCRIPTION OF THE DRAWINGS

A more complete appreciation of the invention and many of the attendant advantages thereof will be readily obtained by reference to the following detailed description when considered in connection with the accompanying drawings, wherein.

DESCRIPTION OF THE PREFERRED EMBODIMENTS

Figure 1:
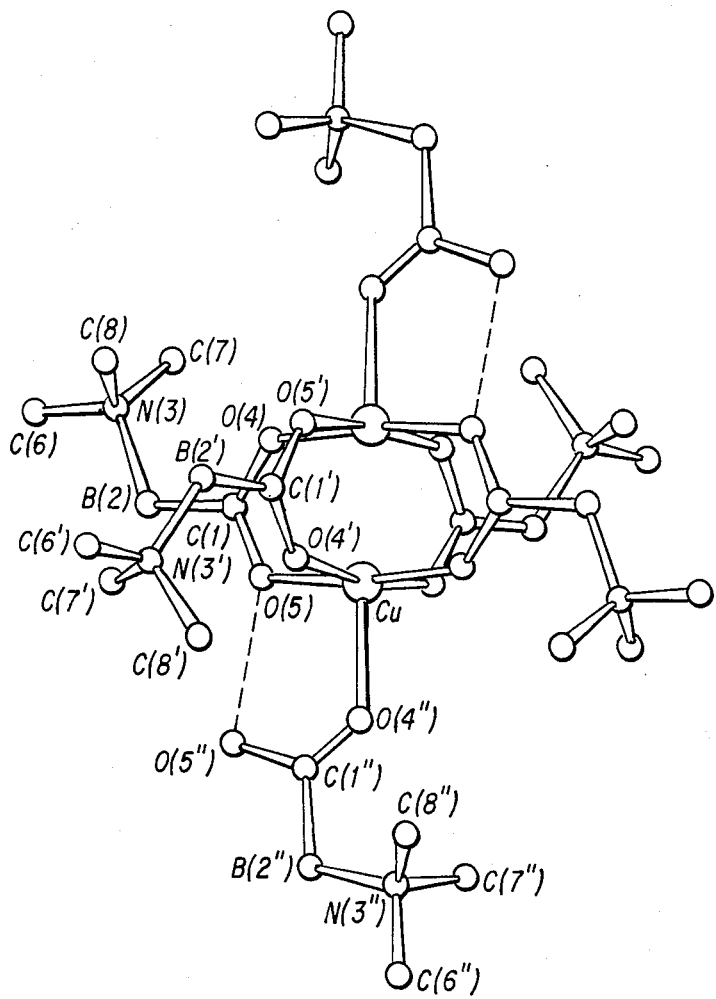
FIG. 1 shows the structure of {Cu[(CH$_3$)$_3$N.BH$_2$CO$_2$]$_2$.(CH$_3$)$_3$N.BH$_2$COOH}$_2$, excluding the hydrogen atoms for clarity, with the atom numbering scheme of the asymmetric crystal unit.

The present invention arose in part from the discoveries that binuclear copper(II) carboxylates could be formed from amine-carboxyboranes and that these compounds had higher pharmacological activities than the amine-carboxyborane compounds from which they were formed. Although binuclear copper(II) carboxylates were previously known [Catterick and Thornton, in *Adv. Inorg. Chem. Radiochem.*, Emelius and Sharpe, Eds., 20:291 (1977)], these compounds had been investigated because of their magnetic and electronic properties rather than because of any known biological activity. Accordingly, the carboxyborane derivatives of the present invention represent a surprising advance in the activity of these compounds.

Binuclear copper(II) carboxylates of the invention are those having the formula $$[Cu(R_3NBH_2CO_2)_2 \cdot L]_2$$

wherein each R independently represents H, $C_1-C_{10}$ alkyl, or phenyl, and L represents a non-toxic Lewis base capable of forming a coordinate bond with the copper with the provisos that any two or three R attached to the same nitrogen may represent a $C_4-C_5$ alkylene group containing up to 2 non-cumulative double bonds optionally having 1 or 2 carbons replaced by oxygen or nitrogen, that any 3 R attached to the same nitrogen when taken together with the nitrogen may represent a 6-membered aromatic ring containing 1, 2 or 3 nitrogen atoms, and that any R containing a carbon atom may be substituted with a hydroxyl, ether, ester, carboxyl, or amino functional group. As is evident from this description, the amine portions of these molecules may represent, among others, pyrrole, pyrazole, imidazole, 2-isoimidazole, isoxazole, piperazine, p-isoxazine, morpholine, 4-azacyclohexanone, pyridine, pyrazine and similar compounds, such as the naturally occurring pyrimidines. Acyclic amines which can be used to form the amine portion of the molecule include ammonia, trimethyl amine, aniline, amino acids and esters of amino acids (especially the naturally occurring amino acids), 2-methoxyethylamine and similar compounds.

Of the possible amines which can be used, those which have relatively small amine portions (especially those in which the amine from which the amino portions is derived has 10 or fewer carbons) are preferred. Among these preferred amines are those wherein each R independently represents hydrogen, $C_1$-$C_4$ alkyl, phenyl, or one of the heterocyclic compounds previously named and the total number of carbons is 10 or fewer. Especially preferred are those amines wherein each R independently represents H or a $C_1$-$C_4$ alkyl.

The binuclear copper(II) carboxylates of the invention can be prepared by dissolving the amine-carboxyborane compound in a basic solution (preferably about 0.4N NaOH) and mixing with a solution of a copper salt, preferably $CuCl_2$, preferably at a concentration of from about 0.1 to about 0.2 molar, most preferably about 0.15 molar, for the amine-carboxyborane and from about 0.05 to 0.1 molar, preferably about 0.075 molar, for copper. If desired, a complex can be formed from a mixture of amine-carboxyboranes formed from different amines. The resulting dark green solution is allowed to evaporate slowly until crystallization occurs, at which time the crystals are collected and washed. The procedure is simple and can be utilized with any soluble copper salt and any amine-carboxyborane. Any other method of forming the copper complex or of forming and collecting crystals thereof may also be used.

Generally speaking, the process described above will produce molecules of the formula $[Cu(amine.BH_2CO_2)\cdot amine.BH_2CO_2H]_2$ when one of the especially preferred small amines of the invention is present in the molecule and molecules of the formula $[Cu(amine.BH_2CO_2)\cdot H_2O]_2$ when a large amine, such as N-methylmorpholine, is present, probably because of steric interactions between the axial ligands and the chelating carboxylates. As is well-understood to those skilled in the art of preparing coordination complexes, however, molecules in which L is a Lewis base which has formed a coordinate bond with the copper atom can be formed by chosing proper conditions (e.g., ratio of reactants) for the formation of the initial complex or by a ligand exchange reaction. For example, many similar binuclear organic carboxylates are known in which various ligands are present in the axial positions. Such ligands include 1-phenyl-2,3-dimethyl-5-pyrazolone (antipyrine), 4-acetylpyridine N-oxide, aniline, 4 bromoaniline, 3-bromopyridine, 3,5-dibromosalicylate, 5-bromosalicylate, 1,4-dioxane, acetylacetonate, 4-chloroaniline, 2-chloropyridine, 4-chloropyridine N-oxide, 5-chlorosalicylate, 2,2-dipyridyl-N, N-dioxide, dimethylformamide, ethylenediamine, 2-ethylpyridine, 5-iodo-salicylate, 2,3-lutidine, 2,6-lutidine, 3-(1-methyl-3-pyrrolidinyl)pyridine (nicotine), 4-nitropyridine N-oxide, $\beta$-naphthoquinoline, triphenylphosphine oxide, 2-picoline, 3-picoline, 4-picoline, 2-picoline N-oxide, 3-picoline N-oxide, 4-picoline N-oxide, 1,2-propanediamine, 1,3-propanediamine, pyridine, pyridine N-oxide, quinoline, isoquinoline, salicylate, 3-toluidine, 4-toluidine, thenoyltrifluoroacetate, and water. Examples of binuclear copper complexes formed from organic carboxylates and these ligands are shown in Melnick, *Coordination Chemistry Reviews*, 36 1–44 (1981) and Catternick and Thornton, *Adv. Inorg. Chem. Radiochem.*, 20, 291–362 (1977), which are herein incorporated by reference. Complexes of the invention, in which the organic carboxylates are replaced with amine-carboxyboranes, can be prepared in the same manner as these complexes formed from organic carboxylates. The only precaution which must be taken is the avoidance of acidic conditions, which result in the dissolution of the binuclear complex as the chelating carboxylate groups of the amine-carboxyboranes become protonated to the corresponding carboxylic acid forms. The pKa of the amine-carboxyboranes, if not already known, can be easily determined by simple experimentation. Examples of typical pKa values are given in Scheller et al, *Inorganica Chemica Acta*, 57, 227–228 (1982), which is herein incorporated by reference, and are generally about 8.1–8.4.

Ligand exchanges are preferably carried out in the ligand as solvent, if the ligand is a liquid, such as an aliphatic alcohol (e.g., methanol) or an organic amine (e.g., aniline). If the ligand being introduced is not a liquid, it may be dissolved in an organic solvent or water along with the existing complex. Excess ligand may be present in order to drive the ligand exchange reaction in the desired direction, but is not necessary. As pointed out in Kettle et al, *J. Chem. Soc. (A)*, 1243–1247 (1968), which is herein incorporated by reference, analytically pure binuclear copper (II) carboxylate complexes of specified stoichiometry can be prepared by reacting an appropriate quantity of ligand L with an initially prepared hydrated complex (i.e., L is $H_2O$) in solution. The same type of reactions can be carried out with compounds of the invention. Similar organic carboxylate complex and methods of producing them which can be used for producing the boron-containing complexes of the invention are disclosed in Moreland and Doedens, *J. Amer. Chem. Soc.*, 97 508–513 (1975) and Valentine et al, *J. Amer. Chem. Soc.*, 96, 97–99 (1974), which are herein incorporated by reference.

Solvents in which ligand exchange reactions or initial formation of the complex may take place depend on the structure of the amine portion of the complex and on the ligand being introduced as is well understood by those skilled in the art. Typical solvents which may be used include water and polar organic solvents, such as methanol and pyridine. Typical of solubilities are the following relative solubilities of $\{Cu[(Me_3NBH_2COO)_2\cdot Me_3NBH_2CO_2H]\}_2$:

| Solvent | Solubility |
| --- | --- |
| Water | very soluble |
| 2-Chloro-2-methylpropane | insoluble |
| Ethanol | very slightly soluble |
| Methanol | moderately soluble |
| Pyridine | moderately soluble |
| Acetic Acid | moderately soluble |
| Tetrahydrofuran | insoluble |
| Acetonitrile | moderately soluble |
| Dimethyl sulfoxide | moderately soluble |
| Benzene | insoluble |
| Diethyl ether | insoluble |
| Methylene chloride | slightly soluble |
| Chloroform | insoluble |
| Acetone | insoluble |
| Isopropanol | insoluble |
| Pentane | insoluble |
| Ethyl Acetate | insoluble |
| Isopropyl ether | insoluble |

Preferred are complexes in which L is $R_3N.BH_2CO_2H$, $H_2O$, a $C_1$-$C_4$ aliphatic alcohol, a $C_1$-$C_4$ aliphatic amine (primary, secondary, or tertiary), analine, or pyridine. Especially preferred for L are $R_3N.BH_2CO_2H$ and $H_2O$ with $R_3N.BH_2CO_2H$ being most preferred.

The synthesis of the amine-carboxyboranes themselves is well-understood and is disclosed in, for example, U.S. Pat. No. 4,312,989 and Spielvogel, "Synthesis and Biological Activity of Boron Analogues of the $\alpha$-Amino Acids and Related Compounds," in *Boron*

*Chemistry*, Parry and Kodama, eds., Pergamon Press, New York, 1981, pages 119-192, which are herein incorporated by reference. Generally, a tertiaryamine-carboxyborane is prepared by hydrolysis of the corresponding amine-cyanoborane, which is itself easily accessible by the reaction of the amine hydrochloride with sodium cyanoborohydride. This reaction is extremely general for trisubstituted amines and places no other limitations on the structure of the amine used in a reaction. Amine-carboxyboranes in which the amine is derived from a primary or secondary amine are more readily synthesized by other methods. These compounds are easily obtained, for example, by an amine exchange reaction. In a typical synthesis, $Me_2NBH_2CO_2H$, prepared as described above, is allowed to react with the primary or second amine (or ammonia) in a closed container over an extended period of time (e.g., about three weeks). Excess amine (or ammonia) is then removed, and the product is purified using standard techniques. This exchange technique is described in copending application Ser. No. 106,416, filed Dec. 21, 1979, which is herein incorporated by reference. In addition to the previously-mentioned publications and patent applications, other publications also disclose and discuss the synthesis of the amine-carboxyboranes. For example, Spielvogel et al [*J. Inorg. Nucl. Chem.*, 41;223 (1979), which is herein incorporated by reference] disclose the formation of amine-cyanoboranes in which the amine is N-methyl morpholine, ethylenediamine, tetramethylethylenediamine, or aniline.

Binuclear copper(II) carboxylates formed from amine-carboxyboranes can be utilized for any of the uses and at any of the dosage rates previously disclosed for amine-carboxyboranes. However, they may also be utilized at lower dosages, since they have higher pharmacological activities. Appropriate pharmacological uses of these compounds include use as anti-inflammatory agents, anti-arthritic agents, anti-hyperlipidemic agents, and anti-neoplastic agents.

The appropriate therapeutically effective dose can be determined readily and will usually be within from about 0.01 mg/kg to about 200 mg/kg of body weight for the animal being treated. When used as anti-hyperlipidemic agents in mammals, the dose is preferably in the range from about 0.5 mg/kg to about 25 mg/kg. More preferably, the dosage is in the range from about 1 to about 10 mg/kg.

Although similar amounts may be used in the treatment of tumors, amounts in the range of from about 2 to about 95 mg/kg being more preferred. Tumors, the growth of which may be suppressed, include those listed in Holland and Frei, *Cancer Medicine,* Lea and Febiger, Philadelphia, 1973, which is herein incorporated by reference. Although treatment of any mammal is encompassed by this invention, treatment of humans is especially preferred.

The mode of administration of compounds of the invention may be by any suitable route which delivers the compound to the system being treated. For the purposes of the present invention, the compounds may be administered orally, topically, parenterally, intraperitoneally, rectally, by inhalation spray, or by any other method which enables the active ingredient to reach the site being treated. The term parenteral as used herein includes subcutaneous, intravenous, intramuscular, intrasternal, and infusion techniques.

Compounds of the invention may be prepared into pharmaceutical compositions containing the active ingredient in a form suitable for any of the usages previously described. For example, a pharmaceutical composition suitable for oral use may be in the form of, for example, a tablet, troche, lozenge, aqueous or oral suspension, dispersible powder or granule, emulsion, hard or soft capsule, syrup, or elixir. Compositions intended for oral use may be prepared according to any method known in the art for the manufacature of pharmaceutical compositions and may contain one or more agents selected from the group consisting of sweetening, flavoring, coloring, and preserving agents. Tablets containing the active ingredient in admixture with non-toxic pharmaceutically acceptable excipients may be prepared by any method suitable for the manufacture of tablets. Excipients may include, for example, inert diluents, such as calcium carbonate or lactose; granulating and disintegrating agents, such as maize starch or algenic acid; binding agents, such as starch and gelatin; and lubricating agents, such as magnesium stearate and talc. The tablets may be uncoated or they may be coated by any known technique to delay disintegration and absorption in the gastrointestinal tract and thereby provide a sustained action over a long period.

Aqueous suspensions containing the active material in admixture with excipients suitable for the manufacture of aqueous suspensions may also be prepared. Such excipients include suspending agents, such as methyl cellulose; dispersing or wetting agents such as lecithin and condensation products of an alkylene oxide with a fatty acid, such as polyoxyethylene stearate; or similar materials. The aqueous suspension may also contain a preservative, such as p-hydroxybenzoate, a coloring agent, a flavoring agent, or a sweetening agent.

Oily suspensions may be formulated by suspending the active ingredient in a vegetable oil or mineral oil. The oil suspensions may contain a thickening agent, such as beeswax. Sweetening agents, flavoring agents, and preserving agents, such as those described above, may also be used.

Other pharmaceutical preparations may be prepared by any of the techniques now known to the pharmaceutical arts.

It is preferred that the compounds of the invention, when in the form of pharmaceutical preparations, are present in unit dosage forms. When intended for human use, these amounts can easily be calculated from the dosage rates previously given by assuming a body weight of 70 kg. Accordingly, a preferred unit-dose-containing pharmaceutical preparation would contain from about 70 to about 700 mg of active ingredient. It will be understood, however, that the specific dose level for any particular patient will depend upon a variety of factors including the activity of the specific compound employed; the age, general health, sex, and diet of the patient; the time of administration; the route of administration; the rate of excretion; possible synergistic effects with any other drugs being administered; and the severity of the particular disease being treated.

The invention now being generally described, the same will be better understood by reference to certain specific examples which are included herein for purposes of illustration only and are not intended to be limiting of the invention or any embodiment thereof, unless specified.

EXAMPLE 1: SYNTHESIS AND DETERMINATION OF STRUCTURE

Experimental Preparation of {Cu[(CH$_3$)$_3$N.BH$_2$CO$_2$]$_2$.(CH$_3$)$_3$N.BH$_2$COOH} [hereinafter Compound I]

Trimethylamine-carboxyborane (1.8703 g, 15.9 mmol) was dissolved in 1N NaOH (16 mL) and H$_2$O (20 mL). Dropwise addition to 23 mL of a solution of CuCl$_2$.2H$_2$O (1.36 g, 8 mmol) in H$_2$O (40 mL) produced a dark green solution which was allowed to stand overnight. Subsequent filtration through a fine fritted funnel removed a greenish sludge and left a dark green filtrate which was then allowed to evaporate slowly in a beaker open to the atmosphere. After 2-3 days, when the solution had evaporated almost to dryness, dark green crystals were filtered off and washed, first with cold CHCl$_3$ and then with warm CHCl$_3$ (40° C.) in a boiling tube immersed in a water bath. The green product crystals were then filtered off, sprinkled sparingly with deionized water to ensure removal of any traces of NaCl, and finally dried in vacuo. The yield was 0.49 g (22%), m.p. 165° C. (dec.); IR: $\nu_{BH}$, 2350, $\nu_{C=O}$ 1665 cm$^{-1}$. Anal. Calc. for C$_{24}$H$_{68}$Cu$_2$B$_6$N$_6$O$_{12}$:Cu, 34.95; H, 8.31; N, 10.19. Found: C, 35.00; H, 8.49; N, 10.15.

Crystal Data. C$_{24}$H$_{68}$Cu$_2$B$_6$N$_6$O$_{12}$, M=824.80, a=21.818(9), b=18.402(7), c=11.287(5) Å, U=4532 Å$^3$, Z=4, D$_c$=1.209 g cm$^{-3}$.

Absorption coefficient for Cu-K$_\alpha$ radiation ($\lambda$=1.5418 Å), $\mu$=16.2 cm$^{-1}$. Space group Pbca (D$_{2h}^{15}$), uniquely determined by the systematic absences: Okl when k$\neq$2n, h0l when l$\neq$2n, hk0 when h$\neq$2n.

Crystallographic Measurements. A crystal of dimensions ca. 0.26 x 0.26 x 0.30 mm was oriented inside a thin-walled glass capillary to rotate about the crystallographic c-axis. Preliminary unit-cell constants and space group information were obtained from oscillation and Weissenberg photographs taken with Cu-K$_\alpha$ radiation. The crystal was then transferred to an Enraf-Nonius CAD-3 automated diffractometer (Ni-filtered Cu-K$_\alpha$ radiation) where one octant of reciprocal space to $\theta$=67° was surveyed by means of the $\theta$-2$\theta$ scanning procedure as described in McFadden and McPhail, *J. Chem. Soc. Dalton Trans.*, 363 (1974). Instrument and crystal stability were monitored throughout by remeasuring the intensity of a reference reflection after each batch of 99 measurements; no significant variation was noted. A total of 1890 reflections for which I>2.0-$\sigma$(I)[$\sigma^2$(I)=scan count+total background count] were judged to be observed and were used in the structure analysis after the usual Lorentz and polarization corrections had been applied. No absorption corrections were necessary. Refined unit-cell parameters were derived by least-squares treatment of the diffractometer setting angles for 40 high order reflections widely separated in reciprocal space.

Structural Analysis. The structure was solved by the heavy-atom method. Copper atom coordinates were derived from a three-dimensional Patterson map, and non-hydrogen atom coordinates were then obtained from F$_o$ and difference Fourier synthesis. Full-matrix least-squares adjustment of positional and thermal (anisotropic Cu, C, N, B, O; isotropic H) parameters converged at R=0.046. Final atomic positions are illustrated by FIG. 1.

Neutral atom scattering factors used in all structure-factor calculations were those for copper, carbon, boron, nitrogen, and oxygen from Cromer and Waber, *Acta Cryst.*, 18 104 (1965), and for hydrogen from Steward et al, *J. Chem. Phys.*, 42 3175 (1965), with that for copper corrected for the real part of anomalous dispersion according to "International Tables for X-ray Crystallography," Vol. III, Kynoch Press, Birmingham, 1962. In the least-squares iterations, $\Sigma w\Delta^2$ ($\Delta = ||F_o|-|F_c||$) was minimized with weights, w being of the form:

$$\sqrt{w}=1 \text{ for } |F_o|\leq 75.0, \sqrt{w}=75.0/|F_o| \text{ for } |F_o|>75.0.$$

with that for copper corrected for the real part of anomalous dispersion according to "International Tables for X-ray Crystallography," Vol. III, Kynoch Press, Birmingham, 1962. In the least-squares iterations, $\Sigma w\Delta^2$ ($\Delta = ||F_o|-|F_c||$) was minimized with weights, w being of the form:

$$\sqrt{w}=1 \text{ for } |F_o|\leq 75.0, \sqrt{w}=75.0/|F_o| \text{ for } |F_o|>75.0.$$

RESULTS AND DISCUSSION

A view of the centrosymmetric {Cu[(CH$_3$)$_3$N•BH$_2$COO]$_2$•(CH$_3$)$_3$N•BH$_2$COOH}$_2$ structure is shown in FIG. 1. Interatomic distances and angles are reported in Table I. Three of the equatorial Cu-O distances [1.958(4)-1.961(4) Å] are essentially equal, whereas that at 1.984(4) Å is significantly longer, and weaker, owing to the involvement of the oxygen atom in an intramolecular hydrogen bond to the neutral axial ligand [O(5) . . . O(5") 2.789(5) Å]. A like variation of equatorial Cu-O lengths is encountered in the [Cu(CH$_3$COO)$_2$.H$_2$O]$_2$ dimer where pairs of distances are present (1.945, 1.950 Å and 1.986, 1.994 Å), the longer pair being to those oxygen atoms which participate in intermolecular hydrogen bonds to the axial water ligands of adjacent dimers. Despite these individual variations, the means of these Cu-O lengths in both dimers are not significantly different, 1.966 Å in the present study and 1.969 Å in [Cu(CH$_3$COO)$_2$.H$_2$O]$_2$. The axial Cu-O length found in the present complex at 2.173(3) Å is significantly shorter than the corresponding distance [2.195(6) Å] in [Cu(CH$_3$COO)$_2$.CH$_3$COOH]$_2$. The Cu . . . Cu intradimer distance at 2.508(1) Å found here is the shortest yet encountered in such copper (II) carboxylate bridged dimers, contrasting with that of 2.616(1) Å in [Cu(CH$_3$COO)$_2$.CH$_3$COOH]$_2$, and it is the first recorded instance for this class of compound where it is less than that of 2.56 Å in copper metal.

TABLE I

| Interatomic Distances (Å) and Angles (°), with Standard Deviations in Parentheses | | | |
|---|---|---|---|
| (a) Around Copper[a] | | | |
| (i) Distances | | | |
| Cu . . . Cu | 2.508(1) | Cu-O(4") | 2.173(3) |
| Cu-O(5) | 1.984(4) | Cu-O(4$^I$) | 1.961(4) |
| Cu-O(4') | 1.958(4) | Cu-O(5'$^I$) | 1.961(4) |
| (ii) Angles | | | |
| O(5)-Cu-O(4') | 86.6(2) | O(4')-Cu-O(4$^I$) | 91.0(2) |
| O(5)-Cu-O(4") | 93.8(1) | O(4')-Cu-O(5'$^I$) | 171.5(2) |
| O(5)-Cu-O(4$^I$) | 171.3(1) | O(4")-Cu-O(4$^I$) | 94.7(1) |
| O(5)-Cu-O(5'$^I$) | 91.8(2) | O(4")-Cu-O(5'$^I$) | 95.1(2) |
| O(4')-Cu-O(4") | 93.3(2) | O(4$^I$)-Cu-O(5'$^I$) | 89.3(2) |
| (b) Within the Ligands | | | |
| Double | | | |

TABLE I-continued

Interatomic Distances (Å) and Angles (°), with Standard Deviations in Parentheses

|  | Unprimed | Primed | Primed |
|---|---|---|---|
| (i) Distances | | | |
| C(1)-B(2) | 1.593(9) | 1.617(11) | 1.599(9) |
| C(1)-O(4) | 1.263(6) | 1.274(7) | 1.224(6) |
| C(1)-O(5) | 1.280(6) | 1.265(7) | 1.335(6) |
| B(2)-N(3) | 1.629(8) | 1.620(10) | 1.60(9)[a] |
| N(3)-C(6) | 1.49(9) | 1.45(10) | 1.498(9) |
| N(3)-C(7) | 1.488(10) | 1.491(10) | 1.488(9) |
| N(3)-C(8) | 1.478(10) | 1.456(9) | 1.476(9) |
| (ii) Angles | | | |
| B(2)-C(1)-O(4) | 121.4(5) | 120.2(5) | 126.2(5) |
| B(2)-C(1)-O(5) | 117.3(5) | 117.5(5) | 115.7(5) |
| O(4)-C(1)-O(5) | 121.2(5) | 122.3(6) | 118.1(5) |
| C(1)-B(2)-N(3) | 113.5(5) | 113.1(6) | 111.1(5) |
| B(2)-N(3)-C(6) | 108.8(5) | 107.3(5) | 107.2(5) |
| B(2)-N(3)-C(7) | 111.9(5) | 110.9(6) | 112.1(5) |
| B(2)-N(3)-C(8) | 110.4(5) | 112.1(5) | 113.0(5) |
| C(6)-N(3)-C(7) | 108.4(6) | 110.0(5) | 108.1(5) |
| C(6)-N(3)-C(8) | 107.9(5) | 107.9(6) | 107.7(5) |
| C(7)-N(3)-C(8) | 109.3(5) | 108.5(6) | 108.6(5) |

[a]The Roman numeral superscript (I) refers to the transformations of the coordinates listed in Table I to equivalent position ($-\underline{x}$, $-\underline{y}$, $-\underline{z}$).

[a]The Roman numeral superscript (I) refers to the transformations of the coordinates listed in Table I to equivalent position ($\underline{x}$, $\underline{y}$, $\underline{z}$).

EXAMPLE 2: ANTIHYPERLIPIDEMIC ACTIVITY

Experimental

Antihyperlipidemic Screens in Normal Rodents

Compounds to be tested were suspended in 1% carboxymethylcellulose-water and administered to $CF_1$ male mice (~25 g) intraperitoneally for 16 days or Holtzman male rats (~350 g) orally by an intubation needle for 16 days. On days 9 or 16, blood was obtained by tail vein bleeding and the serum separated by centrifugation for 3 min. The serum cholesterol levels were determined by a modification of the Liebermann-Burchard reaction as described in Ness et al, *Clin. Chim. Acta*, 10, 229 (1964). Serum was also collected on day 16 and the triglyceride content was determined by a commercial kit, The Fisher Hycel Triglyceride Test Kit.

Testing in Atherogenic Mice $CF_1$ male mice (~25 g) were placed on a commercial diet (the U.S. Biochemical Corporation Basel Atherogenic Test Diet) which contained butterfat (400 g), celufil (cellulose; 60 g), cholesterol (53 g), choline dihydrogen citrate (4 g), salt mixture oil (Wesson; 40 g), sodium cholate (20 g), sucrose (223 g), vitamin free casein (200 g) and total vitamin supplement for 10 days. After the cholesterol and triglyceride levels were assayed and observed to be elevated, the mice were administered test drugs at 10 mg/kg/day intraperitoneally for an additional 12-day period. Serum cholesterol and triglyceride levels were measured after 12 days of administration of the drugs.

Animal Weights and Food Intake

Periodic animal weights were obtained during the experiments and expressed as a percentage of the animal's weight on day 0. After dosing for 14 days with test drugs, selected organs were excised, trimmed of fat and weighed. The organ weights were expressed as a percentage of the total body weight of the animal.

Toxicity Studies

The acute toxicity ($LD_{50}$ values) was determined in $CF_1$ male mice by administering test drugs intraperitoneally from 5–50 mg/kg as a single dose. The number of deaths recorded over 7 days in the group was determined for each dosage.

Enzymatic Studies

In vitro enzymatic studies were determined using 10% homogenates of $CF_1$ male mouse liver with 50–200 $\mu M$ of test drugs. In vivo enzymatic studies were determined using 10% homogenates of liver from $CF_1$ male mice obtained after administering the agents for 16 days at a dose ranging from 2.5–20 mg/kg/day intraperitoneally. The liver homogenates for both in vitro and in vivo studies were prepared in 0.25M sucrose and 0.001M (ethylenedinitrilo)tetraacetic acid. Acetyl coenzyme A synthetase and adenosine triphosphate dependent citrate lyase activities were determined spectrophotometrically at 540 nm as the hydroxylamate of acetyl coenzyme A formed after 30 min at 37° C. Mitochondrial citrate exchange was determined by the procedure of Robinson et al [*Eur. J. Biochem.*, 216, 63 (1970)] using $^{14}C$-sodium bicarbonate (41 mCi/mmol) incorporated into mitochondrial $^{14}C$-citrate after isolating rat mitochondria (9000 g × 10 min) from the homogenates. The exchanges of the $^{14}C$-citrate were determined after incubating the mitochondrial fraction which was loaded with labeled citrate and test drugs for 10 min. Then the radioactivity was measured in the mitochondrial and supernantant fractions in scintillation fluid and expressed as a percentage. Cholesterol side chain oxidation was determined by the method of Kritchevsky and Tepper [*Artherosclerosis*, 18, 93 (1973)] using (26-$^{14}C$) cholesterol (50 mCi/mmol) and mitochondria isolated from rat liver homogenates. After 18 hr incubation at 37° C. with test drugs, the generated $^{14}CO_2$ was trapped in the center well in {2-(2-(p-1,1,3,3,-tetramethylbutylcresoxy)ethoxy]ethyl} dimethylbenzylammonium hydroxide and counted. 3-Hydroxy-3-methylglutaryl coenzyme A reductase (HMG coenzyme A reductase) activity was measured using 1-$^{14}C$-acetate (56 mCi/mmol) and a post-mitochondrial supernatant (9000 g × 20 min) incubated for 60 min at 37° C. [Wada et al, *J. Biochem. (Tokyo)*, 65 71 (1969)]. The digitonide derivative of cholesterol was isolated and counted. Acetyl coenzyme A carboxylase activity was measured by the method of Greenspan and Lowenstein [*J. Biol. Chem.*, 243, 6273 (1968)]. Initially, the enzyme had to be polymerized for 30 min at 37° C. and then the assay mixture containing sodium $^{14}C$-bicarbonate (41.0 mCi/mmol) was added and incubated for 30 min at 37° C. with test drugs. Fatty acid synthetase activity was determined by the method of Brady et al [*J. Biol. Chem.*, 235, 3093 (1960)] using [2-$^{14}C$] malonyl-coenzyme A (37.5 mCi/mmol) which was incorporated into newly synthesized fatty acids that were extracted with ether and counted. Acyl transferase activity was determined with glycerol-3phosphate [L-2-$^{3}H(N)$] (7.1 Ci/mmol) and the microsomal fraction of the liver homogenates [Lamb et al, *Atherosclerosis*, 27, 147 (1977)]. The reaction was terminated after 10 min and the lipids were extracted with chloroform:methanol (1:2) containing 1% conc. HCl and counted. Phosphatidate phosphohydrolase activity was measured as the inorganic phosphate released after 30 min from phosphatidic acid by the method of Mavis et al [*J. Lipid Res.*, 19, 467

(1978)]. The released inorganic phosphate after development with ascorbic acid and ammonium molybdate was determined at 820 nm.

Liver, Small Intestine and Fecal Lipid Extraction

In $CF_1$ male mice that had been administered test drugs for 16 days, the liver, small intestine and fecal materials (24 hr collection) were removed and a 10% homogenate in 0.25M sucrose+0.001M (ethylenedinitrilo)tetraacetic acid was prepared. An aliquot (2 ml) of the homogenate was extracted by the methods of Floch et al [*J. Biol. Chem.*, 226, 497 (1957)] and Bligh and Dyer [*Can. J. Biochem. Physiol.*, 37, 911 (1957)] and the number of mg of lipid weighed. The lipid was taken up in methylene chloride and the cholesterol level triglyceride levels, neutral lipid content and phospholipid content were determined.

$^3$H-Cholesterol Distribution in Rats

Holtzman male rats (~350 g) were administered the test agent for 14 days orally. On day 13, 10 µCi of $^3$H-cholesterol (40.7 mCi/mmol) was administered intraperitoneally in mice and orally in rats, and feces were collected for the next 24 hr. Twenty-four hours after cholesterol administration, the major organs were excised and samples of blood, chyme and urine were obtained. Homogenates (10%) were prepared of the tissues which were combusted and counted. Some tissue samples were plated on Whatman #1 filter paper, dried and digested for 24 hr in base at 40° C. and counted. Results were expressed as dpm/mg of wet tissue and dpm/per total organ.

Cholesterol Absorption Study

Holtzman male rats (~400 g) were administered the test drug orally for 14 days at 10 mg/kg/day. On day 13, 10 µCi of 1,2-$^3$H(N)-cholesterol (40.7 Ci/mmol) was administered to the rat orally. Twenty-four hours later, the blood was collected and the serum separated by centrifugation. Both the serum and the precipitate were counted.

Bile Cannulation Study

Holtzman male rats (~400 g) were treated with test drugs at 10 mg/kg/day orally for 14 days. The rats were anesthetized with chlorpromazine (25 mg/kg) followed in 30 min by pentobarbital (22 mg/kg) intraperitoneally. The duodenum section of the small intestine was isolated, ligatures were placed around the pyloric sphincter and distally to a site approximately one-third of the way down the duodenum. Sterile isotonic saline was injected into the sectioned off duodenum segment. The saline expanded the duodenum and the common bile duct. Once the bile duct was identified, a loose ligature was placed around it, an incision made, and plastic tube introduced into the duct. Once past the ligature, the tubing was tied in place and the ligatures around the duodenum were removed. Once bile was freely moving down the cannulated tube, 1,2-$^3$H(N) cholesterol (40.7 Ci/mmol) was injected intravenously into the rats. The bile was collected over the next 6 hrs and measured (ml). Aliquots were counted as well as analyzed for cholesterol content.

Plasma Lipoprotein Fractions

Holtzman male rats (~400 g) were administered test drugs at 20 mg/kg/day for 14 days. On day 14, blood was collected from the abdominal aorta. Serum was separated from whole blood by centrifugation at 3500 rpm. Aliquots (3 ml) were separated by density gradient ultracentrifugation according to the method of Hatch and Lees [*Adv. Lipid Res.*, 6, 33 (1968)] and Havel et al [*J. Clin. Invest.*, 34, 1395 (1955)] into the chylomicrons, very low density lipoproteins, high density lipoproteins and low density lipoproteins. Each of the fractions was analyzed for cholesterol, triglyceride, neutral lipids, phospholipids and protein levels.

Data are expressed in the Table 2-7 as percent of control ± the standard deviation. The probable significant level (P) between each test group and the control group was determined by the Student's "t" test.

RESULTS

The binuclear copper complex of the invention proved to be a potent hypolipidemic agent after intraperitoneal administration in mice and oral administration in rats (Table II). The reduction of serum cholesterol in mice was dose dependent with 20 mg/kg/day resulting in the maximal effect of 47%. Serum triglyceride levels were reduced greater than 50% at 2.5 and 10 mg/kg/day. In rats at 10 mg/kg/day, similar reduction in serum cholesterol levels was observed as in mice, i.e., 37% reduction. However, in rats at 10 mg/kg/day serum triglyceride levels were reduced 64% which was greater than the 53% reduction in mice at this dose. In hyperlipidemic induced mice, serum cholesterol levels were elevated 183% (354 mg %) above normal values (125 mg %), which were reduced 59% to 148 mg % by drug administration over 12 days. In hyperlipidemic mice, serum triglyceride levels were elevated 168% (367 mg/dl) above control values (137 mg/dl) which were lowered 67% by drug administration to 12/mg/dl.

TABLE II

The Effects of the Binuclear Copper (II) Complex on Serum Cholesterol and Triglyceride Levels of $CF_1$ Male Mice I.P. and Sprague Dawley Rats, Orally

| | % Control | | | | | |
|---|---|---|---|---|---|---|
| | Mice | | | Rats | | |
| | Serum Day 9 | Cholesterol Day 16 | Serum Triglyceride Day 16 | Serum Day 9 | Cholesterol Day 16 | Serum Triglyceride Day 16 |
| (N = 6) Control | $\bar{X}$ ± SD | $\bar{X}$ ± SD | $\bar{X}$ ± SD | $\bar{X}$ ± SD | $\bar{X}$ ± SD | $\bar{X}$ ± SD |
| 1% Carboxymethyl Cellulose Treated | 100 ± 7[b] | 100 ± 6[c] | 100 ± 7[d] | 100 ± 6[e] | 100 ± 6[f] | 100 ± 8[g] |
| 2.5 mg/kg | 61 ± 5[a] | 62 ± 6[a] | 50 ± 6[a] | — | — | — |
| 5.0 mg/kg | 67 ± 6[a] | 63 ± 5[a] | 69 ± 6[a] | — | — | — |
| 10.0 mg/kg | 71 ± 6 | 63 ± 5[a] | 47 ± 5[a] | 63 ± 5[a] | 65 ± 5[a] | 36 ± 4[a] |

TABLE II-continued

The Effects of the Binuclear Copper (II) Complex on Serum Cholesterol and Triglyceride Levels of $CF_1$ Male Mice I.P. and Sprague Dawley Rats, Orally

|  | % Control | | | | | |
|---|---|---|---|---|---|---|
|  | Mice | | | Rats | | |
|  | Serum Day 9 | Cholesterol Day 16 | Serum Triglyceride Day 16 | Serum Day 9 | Cholesterol Day 16 | Serum Triglyceride Day 16 |
| 20.0 mg/kg | 52 ± 5[a] | 53 ± 4[a] | — | — | — | — |

[a] $P \leq 0.001$
[b] 118 mg %
[c] 122 mg %
[d] 137 mg %
[e] 73 mg %
[f] 78 mg %
[g] 110 mg %

Examination of the in vitro liver enzyme studies demonstrated that enzymes involved in the generation of the key intermediate, acetyl coenzyme A required for cholesterol and fatty acid synthesis as well as cholesterol synthesis, were not affected by the presence of the drug (Table III). The degradation of cholesterol by oxidation of the side chain was accelerated significantly (52%) in the presence of drug. Enzyme activities involved in fatty acid synthesis were not affected as well as sn-glycerol-3-phosphate acyl transferase, one of the regulatory enzymes of triglyceride synthesis. However, the other regulatory enzyme of triglyceride synthesis, phosphatidate phosphohydrolase activity, was suppressed with increasing concentration of the drug.

TABLE IV

In Vivo Effects of the Binuclear Copper (II) Complex on $CF_1$ Liver Enzyme Activities after 16 Days Dosing at 10 mg/kg/day, Intraperitoneally

| Control (N = 6) | ATP Dependent Citrate Lyase | Acetyl CoA Synthetase | HMG CoA Reductase | Acetyl CoA Carboxylase | Fatty Acid Synthetase | sn-Glycerol 3-phosphate Acyl Transferase | Phosphatidate Phosphohydrolase |
|---|---|---|---|---|---|---|---|
| 1% Carboxylmethyl Cellulose Treated | 100 ± 7 | 100 ± 8 | 100 ± 8 | 100 + 6 | 100 + 7 | 100 ± 6 | 100 ± 7 |
| 2.5 mg/kg | 70 ± 6[a] | 62 ± 6[a] | 112 ± 8 | 103 ± 6 | 102 ± 7 | 95 ± 6 | 55 ± 5[a] |
| 5.0 mg/kg | 79 ± 7[a] | 77 ± 7[a] | 108 ± 9 | 95 ± | 90 ± 6 | 95 ± 7 | 53 ± 5[a] |
| 10 mg/kg | 72 ± 7[a] | 73 ± 7[a] | 102 ± 8 | 120 ± 7 | 94 ± 5 | 119 ± 7 | 18 ± 3[a] |

[a] $P \leq 0.001$

Studies in vivo after dosing for 16 days in mice (Table IV) showed that there was a moderate suppression of ATP dependent citrate lyase and acetyl coenzyme A synthetase activity at 2.5 mg/kg/day. Phosphatidate Phosphohydrolase activity was reduced in a dose dependent manner with 10 mg/kg/day causing 82% reduction.

Lipid concentrations in rat liver and small intestine were reduced significantly by drug treatment (Table V). The cholesterol, triglyceride, and neutral lipid levels were reduced in both organs and phospholipids were reduced in the small intestine. The lipid content of liver from mice treated 16 days demonstrated similar changes (Table VI), however, more dramatic effects were observed in the lowering of triglyceride levels than cholesterol from 2.5 to 10 mg/kg/day. Higher lipid levels

TABLE III

The Effects of Binuclear Copper Complex (II) on In Vitro $CF_1$ Liver Enzyme Activities

|  | Percent Control ($\overline{X}$ ± SD) | | | |
|---|---|---|---|---|
| Enzyme Parameter (N = 6) | Control | 50 μM | 100 μM | 200 μM |
| Mitochondrial Citrate Exchange | 100 ± 7[c] | 105 ± 6 | 104 ± 6 | 103 ± 7 |
| ATP Dependent Citrate Lyase | 100 ± 6[d] | 110 ± 6 | 98 ± 5 | 105 ± 7 |
| Acetyl CoA synthetase | 100 ± 6[e] | 104 ± 5 | 87 ± 4[b] | 84 ± 5[a] |
| HMG CoA Reductase | 100 ± 9[f] | 102 ± 8 | 101 ± 9 | 105 ± 8 |
| Cholesterol Side Chain Oxidation | 100 ± 5[g] | — | 152 ± 7[a] | — |
| Acetyl CoA Carboxylase | 100 ± 6[h] | 96 ± 6 | 93 ± 5 | 92 ± 5 |
| Fatty Acid Synthetase | 100 ± 8[i] | 86 ± 7 | 96 ± 8 | 87 ± 7 |
| sn-Glycerol-3-phosphate Acyl Transferase | 100 ± 7[j] | 108 ± 6 | 92 ± 8 | 89 ± 6 |
| Phosphatidate Phosphohydrolase | 100 ± 7[k] | 77 ± 5[a] | 63 ± 6[a] | 35 ± 3[a] |

[a] $P \leq 0.001$
[b] $P \leq 0.001$
[c] 30.8% exchange of mitochondrial citrate
[d] 30.5 mg citrate hydrolyzed/gm wet tissue/20 min.
[e] 28.5 mg acetyl CoA formed/gm wet tissue/20 min.
[f] 384,900 dpm cholesterol formed/gm wet tissue/60 min.
[g] 6080 dmp CO$_2$ formed/gm wet tissue/18 hrs.
[h] 32,010 dpm/gm wet tissue/30 min.
[i] 37,656 dpm/gm wet tissue/20 min.
[j] 537,800 dmp/gm wet tissue/20 min.
[k] 16.7 μP$_i$/gm wet tissue/15 min.

were observed in fecal samples of rats after two-week administration of drugs, particularly in the triglyceride, neutral lipid and phospholipid levels (Table V).

After separation of the rat serum lipoprotein fractions (Table IV), it became evident that the cholesterol, neutral lipids and triglyceride content of each fraction was reduced. The phospholipid and protein content of the fractions was not markedly affected by drug treatment.

ally showed reductions in dpm/organ compared to the control, e.g., the liver $^3$H-cholesterol was reduced 42%, the heart 18%, the brain 46% and the kidney 91%. There was higher content of cholesterol in the stomach (198%), chyme (113%), the large intestine (27%), the small intestine (81%) and urine (336%). The LD$_{50}$ in CF$_1$ mice intraperitoneally was 39.2 mg/kg.

DISCUSSION

TABLE V
The Effects of Binuclear Copper (II) Complex on Rat Liver, Small Intestine and Serum Lipoprotein Fraction Lipid Content After 14 Days dosing at 10 mg/kg/day Orally

| | Percent Control ($\bar{X} \pm SD$) | | | | | |
|---|---|---|---|---|---|---|
| | Mg of Lipid Extracted | Cholesterol | Triglyceride | Neutral Lipids | Phospholipids | Protein |
| N = 6 | | | | | | |
| Liver | | | | | | |
| Control | 100 ± 7 | 100 ± 7$^c$ | 100 ± 6$^d$ | 100 ± 6$^e$ | 100 ± 8$^f$ | 100 ± 6$^g$ |
| Treated | 51 ± 5$^a$ | 65 ± 6$^a$ | 76 ± 7$^a$ | 93 ± 9 | 93 ± 9 | 99 ± 7 |
| Small Intestine | | | | | | |
| Control | 100 ± 6 | 100 ± 7$^h$ | 100 ± 5$^i$ | 100 ± 5$^j$ | 100 ± 7$^k$ | 100 ± 7$^l$ |
| Treated | 43 ± 5$^a$ | 47 ± 6$^a$ | 40 ± 4$^a$ | 17 ± 3$^a$ | 46 ± 5$^a$ | 111 ± 8 |
| Feces | | | | | | |
| Control | 100 ± 7 | 100 ± 6$^m$ | 100 ± 6$^n$ | 100 ± 8$^o$ | 100 ± 7$^p$ | 100 ± 5$^q$ |
| Treated | 123 ± 5$^a$ | 110 ± 6 | 133 ± 7$^a$ | 131 ± 7$^a$ | 183 ± 8$^a$ | 68 ± 6$^a$ |
| Lipoprotein Fraction | | | | | | |
| Chylomicrons | | | | | | |
| Control | — | 100 ± 7$^r$ | 100 ± 7$^s$ | 100 ± 8$^t$ | 100 ± 7$^u$ | 100 ± 6$^v$ |
| Treated | — | 88 ± 6 | 58 ± 5$^a$ | 67 ± 7$^a$ | 96 ± 6 | 99 ± 7 |
| VLDL | | | | | | |
| Control | — | 100 ± 6$^w$ | 100 ± 6$^x$ | 100 ± 7$^y$ | 100 ± 8$^z$ | 100 ± 7$^{aa}$ |
| Treated | — | 32 ± 3$^a$ | 43 ± 4$^a$ | 62 ± 5$^a$ | 100 ± 7 | 96 ± 7 |
| LDL | | | | | | |
| Control | — | 100 ± 6$^{bb}$ | 100 ± 7$^{cc}$ | 100 ± 6$^{dd}$ | 100 ± 8$^{ee}$ | 100 ± 8$^{ff}$ |
| Treated | — | 68 ± 6$^a$ | 70 ± 6$^a$ | 78 ± 7$^a$ | 105 ± 6 | 101 ± 6 |
| HDL | | | | | | |
| Control | — | 100 ± 7$^{gg}$ | 100 ± 6$^{hh}$ | 100 ± 7$^{ii}$ | 100 ± 6$^{jj}$ | 100 ± 6$^{kk}$ |
| Treated | — | 64 ± 5$^a$ | 31 ± 5$^a$ | 72 ± 8$^a$ | 86 ± 7 | 108 ± 8 |

$^a$P ≤ 0.001
$^b$P ≤ 0.010
$^c$24.03 mg cholesterol/gm tissue
$^d$44.11 mg neutral lipid/gm tissue
$^e$6.37 mg triglyceride/gm tissue
$^f$7.19 mg phospholipid/gm tissue
$^g$4.5 gm protein/gm wel tissue
$^h$7.83 mg/gm
$^i$6.98 mg/gm
$^j$1.12 mg/gm
$^k$2.06 mg/gm
$^l$42 mg/gm
$^m$28.47 mg/gm
$^n$33.94 mg/gm
$^o$1.86 mg/gm
$^p$1.39 kg/gm
$^q$6.99 mg/gm
$^r$337 µg/ml
$^s$67 µg/ml
$^t$420 µg/ml
$^u$149 µg/ml
$^v$184 µg/ml
$^w$190 µg/ml
$^x$98 µg/ml
$^y$22 µg/ml
$^z$26 µg/ml
$^{aa}$50 µg/ml
$^{bb}$µg/ml
$^{cc}$10 µg/ml
$^{dd}$45 µg/ml
$^{ee}$41 µg/ml
$^{ff}$122 µg/ml
$^{gg}$544 µg/ml
$^{hh}$620 µg/ml
$^{ii}$27 µg/ml
$^{jj}$153 µg/ml
$^{kk}$657 µg/ml

TABLE VI
The In Vivo Effects of the Binuclear Copper (II) Complex on CF$_1$ Mouse Liver Content After 16 Days Dosing

| Control (N = 6) | Mg of Lipid | Cholesterol | Triglycerides | Neutral Lipids | Phospholipids | Protein |
|---|---|---|---|---|---|---|
| 1% Carboxymethyl Cellulose Treated | 100 ± 6 | 100 ± 7$^c$ | 100 ± 5$^d$ | 100 ± 6$^e$ | 100 ± 7$^f$ | 100 ± 5$^g$ |
| 2.5 mg/kg | 82 ± 5$^a$ | 71 ± 6$^a$ | 40 ± 3$^a$ | 79 ± 5$^a$ | 67 ± 6$^a$ | 105 ± 6 |
| 5.0 mg/kg | 85 ± 6$^b$ | 74 ± 7$^a$ | 38 ± 4$^a$ | 86 ± 5$^b$ | 92 ± 7 | 92 ± 5 |
| 10.0 mg/kg | 95 ± 6 | 77 ± 7$^a$ | 36 ± 5$^a$ | 87 ± 4$^b$ | 152 ± 8$^a$ | 101 ± 8 |

$^a$P ≤ 0.001
$^b$P ≤ 0.010
$^c$12.24 mg cholesterol/gm tissue
$^d$4.77 mg triglyceride/gm tissue
$^e$28.35 mg neutral lipid/gm tissue
$^f$4.39 mg phospholipid (P)/gm tissue
$^g$4.5 mg of protein/gm tissue The adsorption of $^3$H-cholesterol after its being administered orally (Table VII) was reduced 85% over a 24-hr period in rats treated 14 days. $^3$H-Cholesterol distribution in major organs after drug therapy gener- The copper complex of the invention was found to be a potent hypolipidemic agent in mice and rats. However, its mode of action seems to be somewhat different from reported amine-cyanoborane and amine-carboxyborane analogues in that HMG CoA reductase and fatty acid synthetase activities were essentially unaltered both in the in vivo and in vitro studies. The binuclear copper (II) complex was active in the dose range previously reported for boron derivatives as hypolipidemic agents [Hall et al, *J. Pharm. Sci.*, 70, 339 (1981)]; nevertheless, it was more potent than commercially available clofibrate which at doses of 150–200 mg/kg lowers serum cholesterol 6–15% and serum triglyceride levels, 25%.

TABLE VII

The Effects of Binuclear Copper Complex (II) on Rat Organs Weights and Orally Administered $^3$H—Cholesterol After Dosing for 14 Days at 10 mg/Kg/Day

| Organ (N = 6) | Organ Weight (gm) | | DPM/Total Organ | |
|---|---|---|---|---|
| | Control | Treated | Control | Treated |
| Brain | 1.866 | 1.666 | 29,115 | 15,783 |
| Lung | 1.766 | 1.933 | 15,350 | 17,106 |
| Heart | 1.333 | 1.021 | 24,582 | 20,060 |
| Liver | 12.000 | 10.600 | 47,429 | 27,695 |
| Kidney | 2.900 | 2.167 | 5,875 | 565 |
| Spleen | 0.566 | 0.501 | 19,388 | 13,241 |
| Adrenal | 0.036 | 0.031 | — | — |
| Stomach | 2.066 | 1.766 | 11,375 | 33,901 |
| Small Intestine | 8.333 | 6.433 | 15,291 | 16,514 |
| Large Intestine | 4.100 | 4.233 | 47,109 | 59,665 |
| Chyme | 5.866 | 5.9333 | 102,772 | 218,742 |
| Feces | 5.702 | 8.633 | 320,454 | 294,644 |

Not only is the binuclear copper (II) complex active orally and intraperiteoneally, it is effective in hyperlipidemic mice, lowering serum cholesterol levels to near normal levels and serum triglyceride levels below normal values after 12 days administration. Although the inventors do not wish to be limited to theory, the mode of action of this agent appeared to be interference with cholesterol absorption from the gastrointestinal tract and accelerated excretion of cholesterol via the fecal route. Triglyceride levels appear to be reduced due to suppression of activity of regulatory enzyme of de novo triglyceride synthesis. Lamb et al [op. cit.] have shown a positive correlation between lowering of serum triglyceride levels and the inhibition of hepatic and intestinal phosphatidate phosphohydrolase activity with 1-methyl-4-piperidyl bis-(p-chlorophenoxy)acetate and 1,3-bis(p-methyl phenoxy)-2-propane. Similar findings have also been made with phthalamide, saccharin, and 1,8-napthalamide cyclic imide derivatives using mouse liver. These compounds as well as clofibrate also suppressed sn-glycerol $^3$-phosphate acyl transferase activity, whereas the binuclear copper complex (II) did not. Clofibrate does accelerate cholesterol excretion via biliary route, however, its effects on liver metabolism include inhibition of HMG CoA reductase activity. Thus the copper complex appears to be different in its mode of action from standard therapeutic agents on the market today, e.g., clofibrate and cholestyramine.

The serum lipoprotein fractions after 14 days dosing at 10 mg/kg/day demonstrated consistent reductions in cholesterol, triglyceride and neutral lipid content. Supposedly, the chylomicrons and very low density fractions contain the highest of triglyceride levels which the binuclear complex (II) reduced significantly. The low and high density lipoprotein fractions contain the majority of the cholesterol and its esters under normal conditions. The cholesterol content of the low density fraction is important in controlling the amount of cholesterol being deposited in atherogenic plaques. Supposedly the high density fraction returns the cholesterol from peripheral tissue to the liver. The binuclear copper complex (II) reduces cholesterol approximately equal in both the low and high density lipoprotein fractions. Thus, probably the ratio of cholesterol content of LDL to HDL fractions has not been altered by drug therapy; however, the absolute content of each fraction has been reduced significantly.

Lipids removed from the serum were not deposited in the organs as demonstrated by reduced lipid content in liver, and small intestine, $^3$H-cholesterol content of the major organs examined and the weights of the organs. This is particularly advantageous since many known agents which reduce serum lipid levels merely transfer the lipids to organs. Adrenal weights were not altered by drug administration, indicating that there was no compensatory hyperplasia of the adrenal cortex due to stimulation of steroidogenesis due to low serum levels. Appetite of the animal was reduced by the compound of the invention, a particularly desirable property for an antihyperlipidemic agent. Suppression of appetite is not a property of the corresponding amine-carboxyboranes.

EXAMPLE 3: ANTINEOPLASTIC ACTIVITY

Experimental

Biological

CF$_1$ male mice (~30 g) were implanted with 2×10$^6$ Ehrlich ascites tumor cells, intraperitoneally on Day 0. Compound I was suspended by homogenation in 0.05% polysorbate.80-water and administered intraperitoneally at 10 and 20 mg/kg for 9 days to determine its effectiveness for inhibition of tumor growth. Mice were sacrificed on Day 10, and the ascites fluid was collected from the peritoneal cavity. The volume and ascrit (packed cell volume) were determined for each animal and the percent inhibition of tumor growth was calculated. For the metabolic studies, mice were treated on Days 8 and 9 with 10 mg/kg of Compound I, intraperitoneally. The animal was sacrificed on Day 10 and the ascites fluid harvested. The in vitro metabolic studies were performed at 0.25, 0.50 and 1 mmol final concentration of Compound I.

In vitro incorporation of $^3$H-thymidine, $^3$H-uridine, or $^3$H-leucine was determined using 10$^6$ Ehrlich ascites cells, 1 μCi labeled precursor, minimum essential medium and varying final concentrations of drug from 0.25–1.0 mM. The tubes were incubated at 37° C. for 60 min and inactivated by trichloroacetic acid. The acid insoluble labeled deoxyribonucleic acid was collected on GF/F glass filter discs and ribonucleic acid and protein were precipitated on nitrocellulose filters by vacuum suction. Results are expressed as dpm of incorporated precursor per hour per 10$^6$ cells.

For in vivo studies, incorporation of thymidine into deoxyribonucleic acid was determined by the method of Chae et al [*Proc. Am. Assoc. Cancer Res.*, 9, 44 (1968)]. One hour prior to the animal sacrifice on Day 10, 10 μCi of 6-$^3$H-thymidine (21.5 Ci/mmol) were injected intraperitoneally. The deoxyribonucleic acid was isolated and the tritium content was determined in a toluene based scintillation fluid. The deoxyribonucleic acid concentration was determined by the diphenylamine reaction using calf thymus deoxyribonucleic acid as a standard. Uridine incorporation into ribonucleic acid was determined using 10 μCi of 5,6-$^3$H-uridine (22.4 Ci/mmol). Ribonucleic acid was extracted by the method of Wilson et al [*Biochem. Biophys. Acta.*, 378, 260 (1975)]. Using yeast ribonucleic acid as a standard, the ribonucleic acid content was assayed by the orcinol reaction. Leucine incorporation into protein was determined by the method of Sartorelli [Biochem. Biophys. Res. Comm., 27, 26 (1967)] using 10 μCi of 4,5-$^3$H-leucine (52.2 Ci/mmol). Protein content was determined by the Lowry procedure using bovine serum albumin as a standard.

In vitro and in vivo nuclear deoxyribonucleic acid polymerase activity was determined on isolated Ehrlich ascites cell nuclei. The incubation was that described by Sawada et al [Can. Res., 34, 3341 (1974)] except that [methyl-$^3$H] deoxythymidine triphosphate (82.4 Ci/mmol) was used. The acid insoluble nucleic acid was collected on GF/F filters and counted. Nuclear ribonucleic acid polymerase activities were determined on enzymes isolated from nuclei. Messenger, ribosomal and transfer ribonucleic acid polymerase enzymes were isolated using, respectively, 0.3M, 0.04M and 0.0M concentration of ammonium sulfate in magnesium chloride. The incubation medium was that of Anderson et al [Biochem. Biophys. Acta, 383, 56 (1975)] using $^3$H-uridine triphosphate (23.2 Ci/mmol). The acid insoluble ribonucleic acid was collected on nitrocellulose filters and counted.

Deoxythymidine as well as deoxythymidylate monophosphate and diphosphate kinase activities were measured spectrophotometrically at 340 nm at 30 min using reduced nicotinamide adenine dinucleotide (0.1 μmole). Thymidine incorporation (6-$^3$H - 21.5 Ci/mmol) into nucleotides was measured using the medium of Maley and Ochoa [J. Biol. Chem., 223, 1538 (1958)]. The reaction medium was extracted with ether and the aqueous layer plated on PEI cellulose F plates and eluted with 0.5N formic acid: 0.6M LiCl (1:1). Areas which correlated with Rf values of thymidine, thymidylate monophosphate, diphosphate and triphosphate standards were scraped and counted.

Carbamyl phosphate synthetase activity was determined using the reaction medium of Kalman et al [Am. Biol. Chem., 24, 1871 (1966)] in the presence of ornithine and ornithine transcarbamylase. Citrulline formed from ornithine was measured at 490 nm by the method of Archibald [J. Biol. Chem., 156, 121 (1944)]. Aspartate transcarbamylase activity was assayed using the incubation medium of Kalman et al [op. cit.]. The colorimetric determination of carbamyl aspartate was conducted by the procedure of Koritz and Cohen [J. Biol. Chem., 209, 145 (1954)]. Orotidine monophosphate decarboxylase activity was assayed by the method of Appel [J. Biol. Chem., 243, 3929 (1968)] using 0.1 μCi of $^{14}$C-orotidine monophosphate (34.9 mCi/mmol). The $^{14}$CO$_2$ generated in 15 min was trapped in 1M KOH and counted. Thymidylate synthetase activity was determined using a post-mitochondrial supernatant (9000 g×10 min) and 5 μCi of 5-$^3$H-deoxyuridine monophosphate (14 Ci/mmol) according to the method of Kampf et al [J. Med. Chem., 19, 903 (1976)]. $^{14}$C-Formate incorporation into purines was determined by the method of Spassova et al [Biochem. Pharmacol., 25, 923 (1976)] using 0.5 μCi of $^{14}$C-formic acid (52.0 mCi/mmol). Purines were separated on silica gel TLC plates eluted with n-butanol-acetic acid-water (4:1:5). After identifying Rf values consistent with the standards adenine and guanine, the plates were scraped and the radioactive content determined. Phosphoribosyl-1-pyrophosphate amidotransferase activity was determined on a supernatant fraction (600 g×10 min) measuring the reduction of 0.6 μmol of nicotinamide adenine dinucleotide at 340 nm for 30 min. Inosinic acid dehydrogenase activity was determined using 8-$^{14}$C-inosine-5'-monophosphate (61 mCi/mmol) and a 7000 g supernatant. A sample of the reaction medium was plated on PEI cellulose F plastic precoated TLC plates and eluted with 0.5M NH$_4$SO$_4$. The Rf value for xanthine monophosphate was scraped and counted. Dihydrofolate reductase activity was determined at 340 nm for 30 min as the oxidation of reduced nicotinamide adenine dinucleotide phosphate. Ribonucleotide reductase activity was determined using 5-$^3$H-cytidine-5'-diphosphate (25 Ci/mmol). Ribose and deoxyribose nucleotide were separated on PEI cellulose F plastic precoated TLC plates eluted with 4% boric acid:4M LiCl (4:3) and scraped at the Rf values consistent with the standard deoxycytidine diphosphate.

An in vitro method was used to determine if compound I was an initiation or an elongation inhibitor of Ehrlich ascites lysate protein synthesis by comparing inhibition with known standards, pyrocateochol violet and emetine, using 1 μCi $^3$H-leucine (24.7 Ci/mmol). The reaction medium was spotted on Whatman #1 filter paper disks, which after drying were treated for 10 min in boiling 5% trichloroacetic acid, for 10 min in cold 5% trichloroacetic acid and washed with cold 5% trichloroacetic acid, ether/ethanol (4:1) and ether. The disks were dried and counted.

RESULTS

Compound I effectively inhibited Ehrlich ascites carcinoma growth at 10 and 20 mg/kg/day with the 10 mg/kg dose affording the higher inhibition of growth, i.e. 99.7% (Table VII).

TABLE VII

The Antieoplastic Activity of Cu[(CH$_3$)$_3$NBH$_2$CO$_2$]$_2$.CH$_3$H.BH$_2$COOH$_2$ (I) Against Ehrlich Ascites Carcinoma Growth in CF$_1$ Male Mice

| Compound | No. of Animals | No. of Animals Survived on Day 10 | Vol(ml) Ascites Fluid | Ascrit Packed Cell Vol. | Percent Inhibition |
|---|---|---|---|---|---|
| Control-0.05% polysorbate.80 | 6 | 6 | 7.17 | 39.3 | — |
| Compound I - 10 mg/kg/day | 6 | 5 | 0.04 | 18.5 | 99.7 |
| Compound II - 20 mg/kg/day | 6 | 6 | 0.32 | 34.0 | 96.2 |
| Standard - 6-mercaptopurine | 6 | 6 | 0.10 | 2.5 | 99.9 |

For the in vivo incorporation studies, the results of which are shown in Table IX, the control values for 10 day Ehrlich ascites cells for thymidine incorporation into deoxyribonucleic acid for 60 min was 107,533 dpm/mg of isolated deoxyribonucleic acid which was inhibited 57% by compound I. For uridine incorporation, the control was 51,193 dpm/mg of ribonucleic acid isolated which was unaffected by drug treatment. Leucine incorporation into protein for the control was 19,181 dpm/mg of isolated protein which was inhibited 52% by drug therapy. Formate incorporation into purine for the 10 day control was 28,786 dpm/mg of protein. Purine de novo synthesis was inhibited 41% by compound I. It may be noted that drug administration for two days reduced the number of cells in the ascites fluid from $226 \times 10^6$/ml to $102 \times 10^6$/ml.

$^{14}CO_2$ generated in 15 min/mg of protein which was not affected by drug administration. Thymidylate synthetase activity for the control was 103,328 dpm/mg of protein which was suppressed 5% by compound I. $^3$H-Thymidine incorporation into thymidylate mono-

TABLE IX

The In vivo Effects of $[Cu[(CH_3)_3NBH_2CO_2]_2 \cdot (CH_3)_3N \cdot BH_2COOH_2]$ at 10 mg/kg/day I.P. on Ehrlich Ascites Carcinoma of $CF_1$ Male Mice

| Biochemical Parameter of Enzyme (N = 6) | % Control Control 0.05% Polysorbate.80 X ± S.D. | Compound I 10 mg/kg/day on Days 8 and 9 X ± S.D. |
|---|---|---|
| $^3$H—Thymidine incorporation into deoxyribonucleic acid | 100 ± 8 | 43 ± 5 |
| $^3$H—Uridine incorporation into ribonucleic acid | 100 ± 9 | 116 ± 10 |
| $^3$—H—Leucine incorporation into protein | 100 ± 8 | 48 ± 6* |
| $^{14}$C—Formate incorporation into purines | 100 ± 12 | 59 ± 6* |
| Number of cells × $10^6$/ml ascites fluid | 100 ± 9 | 45 ± 4* |
| Deoxyribonucleic acid polymerase activity | 100 ± 6 | 38 ± 5* |
| Messenger ribonucleic acid polymerase activity | 100 ± 8 | 96 ± 9 |
| Ribosmoal ribonucleic acid polymerase activity | 100 ± 9 | 96 ± 11 |
| Transfer ribonucleic acid polymerase activity | 100 ± 10 | 63 ± 7* |
| Riboncleotide reductase activity | 100 ± 6 | 101 ± 8 |
| Phosphoribosyl pyrophosphate amido-transferase activity | 100 ± 9 | 41 ± 3* |
| Inosinic acid dehydrogenase activity | 100 ± 10 | 100 ± 9 |
| Dihydrofolate reductase activity | 100 ± 8 | 75 ± 6* |
| Carbamyl phosphate synthetase activity | 100 ± 10 | 77 ± 8* |
| Aspartate transcarbamylase activity | 100 ± 9 | 89 ± 8 |
| Orotidine monophosphate decarboxylase activity | 100 ± 10 | 106 ± 9 |
| Thymidylate synthetase activity | 100 ± 9 | 102 ± 9 |
| Thymidylate monophosphate levels | 100 ± 10 | 43 ± 6* |
| Thymidylate diphosphate levels | 100 ± 12 | 89 ± 11 |
| Thymidylate triphosphate levels | 100 ± 9 | 90 ± 10 |

*P = <0.001

Nuclear deoxyribonucleic acid polymerase activity for the control was 76,528 dpm/hr/mg of nucleoprotein which was reduced 62% by administration of compound I. Nuclear messenger ribonucleic acid polymerase activity for the control was 4,867 dpm/hr/mg of nucleoprotein, ribosomal ribonucleic acid polymerase activity was 8,751 dpm/hr/mg of protein and transfer ribonucleic acid polymerase activity was 10,792 dpm/mg of protein. Messenger and ribosomal ribonucleic acid polymerase activity were not affected by drug administration but transfer ribonucleic acid polymerase activity was suppressed 37%. Ribonucleotide reductase activity for the 10 day control was 153,791 dpm/mg of protein which was unaffected by drug administration.

Phosphoribosyl pyrophosphate amido transferase activity for the control resulted in a net change of 0.544 optical density units/hr/mg of protein. Drug administration for 2 days reduced the activity 59%. Inosinic acid dehydrogenase activity for the control was 36,530 dpm/mg of protein which was essentially not affected by drug therapy. Dihydrofolate reductase activity for 10 day Ehrlich ascites cells was 0.514 optical density units/hr/mg of protein which was inhibited 25% by compound I. Carbamyl phosphate synthetase activity for the control was 0.128 mg of carbamyl phosphate formed/hr/mg/protein which was reduced 23% by compound I. Aspartate carbamyl transferase activity for the control was 7.526 mg of carbamyl aspartate formed/hr/mg of protein which was suppressed 11% by drug administration. Orotidine monophosphate decarboxylase activity for the control was 10,775 dpm of phosphate pool was reduced 57% and TDP and TTP pools were reduced 19% and 10%, respectively. Deoxyribonuclease activity for the control was 247 μg of deoxyribonucleic acid hydrolyzed/hr/mg of protein.

Preliminary whole cell in vitro incorporation studies demonstrated that compound I afforded an $ID_{50}$ value of 0.94 mM concentration for the inhibition of deoxyribonucleic acid synthesis. For ribonucleic acid synthesis the $ID_{50}$ value was 1.82 mM and for the protein synthesis the $ID_{50}$ value was 0.863 mM. (FIG. 2 demonstrates the in vitro effects of compound I on the incorporation studies for nucleic acid, protein and purine biosynthesis.) Using a supernatant fraction, the $ID_{50}$ value for formate incorporation into purine for compound I resulted in an $ID_{50}$ value of 1.71 mM. Deoxyribonucleic acid polymerase activity in isolated nuclei from Ehrlich ascites cells was inhibited significantly by compound I with an $ID_{50}$ valuie of 0.454 mM. Transfer ribonucleic acid polymerase activity resulted in an $ID_{50}$ value of 0.433 mM. Phosphoribosyl pyrophosphate amido-transferase activity was also significantly inhibited by the copper complex with an $ID_{50}$ value of 0.523 mM. Deoxyribonuclease activity was inhibited significantly with an $ID_{50}$ value of 0.682 mM. A number of other enzymes were not inhibited in the concentration range of 0.25 to 1.0 mM by compound I. These include carbamyl phosphate synthetase, aspartate carbamyl transferase, orotidine monophosphate decarboxylase, thymidylate synthetase, inosinic acid dehydrogenase, dihydrofolate reductase, ribonucleotide reductase, messenger and ribosomal ribonucleic acid polymerase activities.

Figure 2:
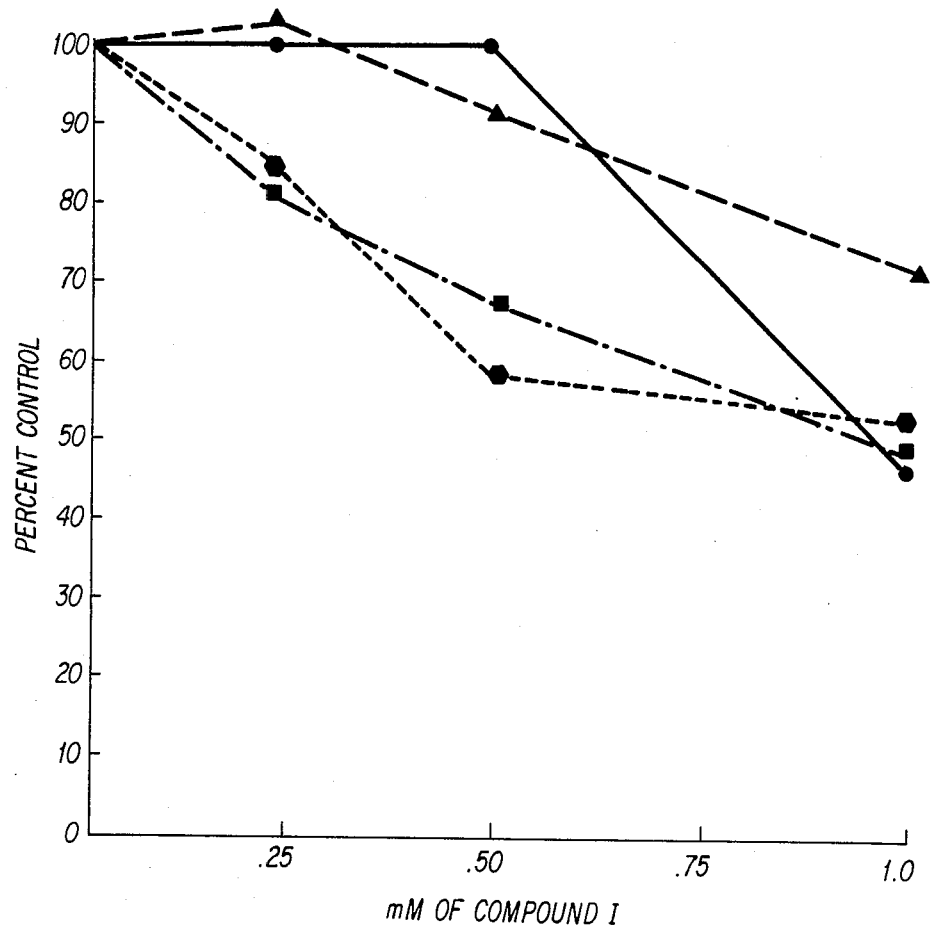
FIG. 2 shows a plot of the in vitro effects of the compound of FIG. 1 on the incorporation of radiolabeled precursors into DNA, RNA, protein, and purine of Ehrlich ascites cells, wherein ●——● represents thymidine incorporation into deoxyribonucleic acid, 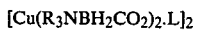 represents uridine incorporation into ribonucleic acid, ■——■ represents leucine incorporation into protein, and ◆——◆ represents formate incorporation into purines.
Figure 3:
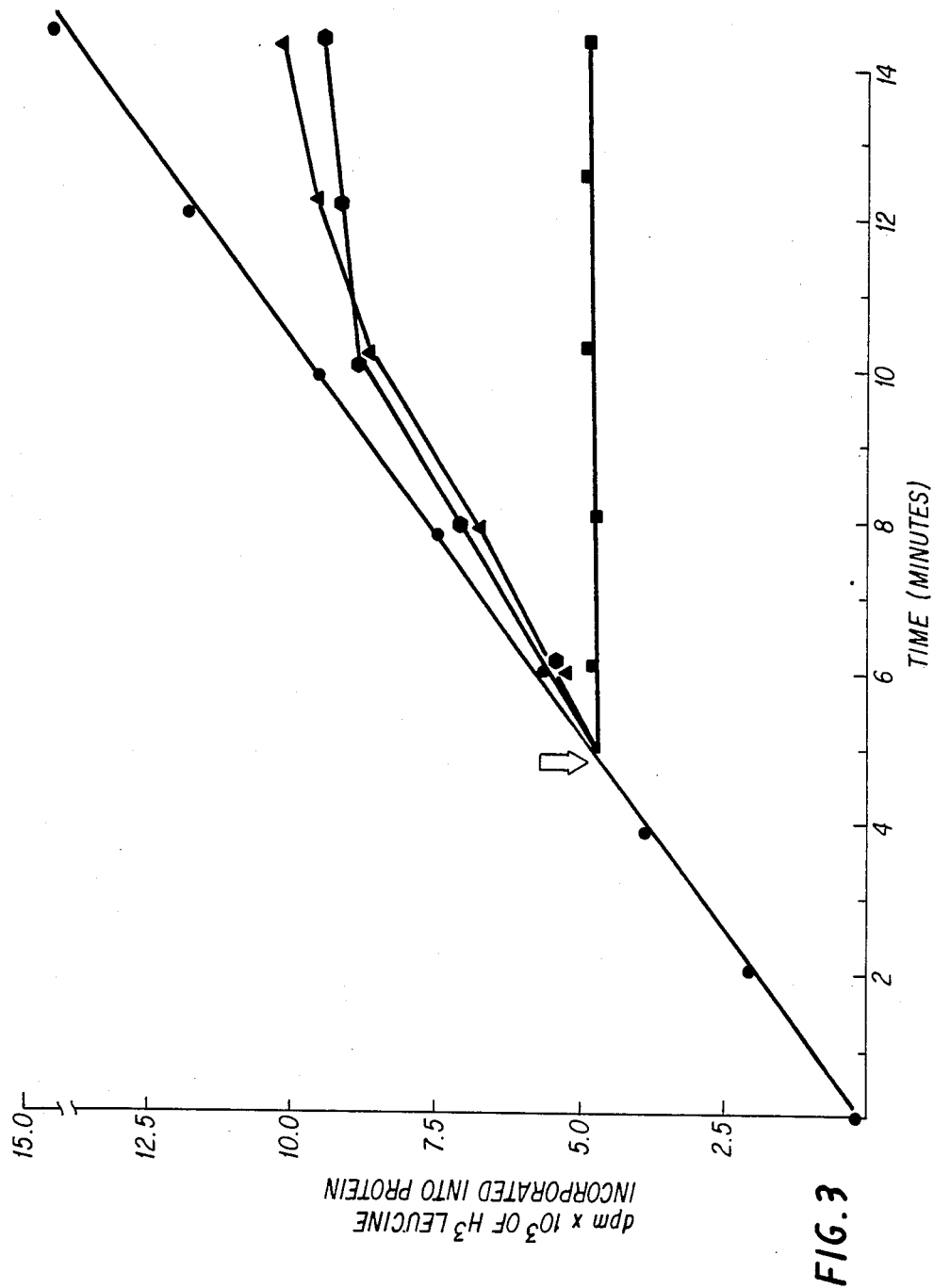
FIG. 3 is a graph showing the effects of the compound of FIG. 1 on the initiation and elongation of protein synthesis by Ehrlich ascites cells, wherein ●—● represents control, ●——● represents pyrocatechol violet, ■—■ represents emetine, 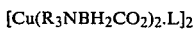 represents Compound 1, and represents the point at which drugs were added.

FIG. 2 demonstrates that compound I does not immediately inhibit protein synthesis of Ehrlich ascites lysates, but rather there is a lag of several minutes before inhibition is observed. Protein synthesis inhibition by compound I resembles more closely the type of inhibition seen for pyrocatechol violet, an initiation inhibitor, rather than that by emetine, an elongation inhibitor of polypeptide synthesis.

DISCUSSION

These results demonstrate that compounds of the invention significantly inhibit deoxyribonucleic acid and protein synthesis in Ehrlich ascites cells. The major sites in deoxyribonucleic acid synthesis which were inhibited include deoxyribonucleic acid polymerase and purine de novo snythesis. The regulatory enzyme was of a magnitude to account for the observed inhibition of purine biosynthesis, phosphoribosyl pyrophosphate amidotransferase was significantly inhibited by compound I, as was the inhibition of purine synthesis. The trimethylamine cyanoboranes and carboxyboranes have previously been observed to inhibit deoxyribonucleic acid polymerase activity in a similar manner as compound I. However, the former derivatives also significantly suppressed thymidylate synthetase activity, but compound I had no effect on thymidylate synthetase activity either in vivo or in vitro.

Compound I moderately inhibited (23%) the regulatory enzyme of pyrimidine synthesis, i.e. carbamyl phosphate synthetase. Moderate inhibition of dihydrofolate reductase by compound I was observed and may be important in one carbon transfer in the synthesis of both purines and pyrimidines. Previous studies with trimethylamine cyanoboranes and carboxyboranes have shown that one carbon transfer from S-adenosyl methionine was suppressed. Deoxyribonuclease activity was also suppressed which indicates that compound I did not cause the release of hydrolytic enzymes from lysosomes and thus cause the degradation of nucleic acids.

The data for the protein experiment demonstrate that compounds of the invention are effective initiation inhibitors of Ehrlich ascites protein synthesis since compound I was shown to behave in the studies similar to the initiation inhibitor, pyrocatechol violet.

The invention now being fully described, it will be apparent to one of ordinary skill in the art that many changes and modifications can be made thereto without departing from the spirit or scope of the invention as set forth herein.

What is claimed as new and desired to be secured by Letters Patent of the United States is:

1. A compound of the formula $[Cu(R_3NBH_2CO_2)_2 \cdot L]_2$ wherein each R independently represents H, $C_1$–$C_{10}$ alkyl, or phenyl and L represents a non-toxic Lewis base capable of forming a coordinate bond with said Cu, with the provisos that any two or three R attached to the same nitrogen may represent a $C_4$–$C_5$ alkylene group containing up to 2 non-cumulative double bonds optionally having 1 or 2 carbons replaced by oxygen or nitrogen, that any 3 R attached to the same nitrogen when taken together with the nitrogen may represent a 6-membered aromatic ring containing 1, 2 or 3 nitrogen atoms, and that any R containing a carbon atom may be substituted with a hydroxyl, ether, ester, carboxyl, or amino functional group.

2. The compound of claim 1, wherein each R is selected to provide a compound in which that portion of each molecule represented by the formula $R_3N$ contains 10 or fewer carbon atoms.

3. The compound of claim 1, wherein each R of each $R_3N$ is H or a $C_1$–$C_4$ alkyl group.

4. The compound of claim 1, wherein L is $R_3NBH_2CO_2H$, $H_2O$, $NH_3$, a $C_1$–$C_4$ aliphatic alcohol, pyridine, aniline, or a primary secondary, or tertiary aliphatic amine in which each alkyl group contains 1–4 carbon atoms.

5. The compound of claim 4, wherein each R is selected to provide a compound in which that portion of each molecule represented by the formula $R_3N$ contains 10 or fewer carbon atmoms.

6. The compound of claim 4, wherein each R of each $R_3N$ is H or a $C_1$–$C_4$ alkyl group.

7. The compound of claim 6, wherein L is $R_3NBH_2CO_2H$ or $H_2O$.

8. The compound of claim 7, having the formula $\{Cu[(CH_3)_3N \cdot BH_2CO_2]_2 \cdot (CH_3)_3N \cdot BH_2COH\}_2$.

* * * * *

UNITED STATES PATENT AND TRADEMARK OFFICE
CERTIFICATE OF CORRECTION

PATENT NO. : 4,550,186

DATED : OCTOBER 29, 1985

INVENTOR(S) : ANDREW T. McPHAIL, BERNARD F. SPIELVOGEL, IRIS H. HALL

It is certified that error appears in the above-identified patent and that said Letters Patent is hereby corrected as shown below:

In abstract, delete "$[Cu(R_3NBH_2CO_2)_2 \cdot R_3NBH_2CO_2H]_2$" and insert --$[Cu(R_3NBH_2CO_2)_2 \cdot L]_2$--;

In column 1, line 21, delete ":" and insert --,--;

In column 1, line 22, delete ":" and insert --,--;

In column 1, line 23, delete ":" and insert --,--;

In column 1, line 68, delete "-N·B-" and insert --NB--;

In column 2, line 8, delete "◄───►" and insert --◄----►--;

In column 2, line 16, delete "──►" and insert --◄──►--;

In column 2, line 17, delete "and represents" and insert --and ──► represents--;

In column 2, line 30, delete ":" and insert --,--;

UNITED STATES PATENT AND TRADEMARK OFFICE
CERTIFICATE OF CORRECTION

PATENT NO. : 4,550,186
DATED : OCTOBER 29, 1985
INVENTOR(S) : ANDREW T. McPHAIL, BERNARD F. SPIELVOGEL, IRIS H. HALL

It is certified that error appears in the above-identified patent and that said Letters Patent is hereby corrected as shown below:

In column 3, line 25, delete "$[Cu(amine.BH_2CO_2)-.amine.BH_2CO_2H]_2$" and insert --$[Cu(amine.BH_2CO_2)_2.amine.BH_2CO_2H]_2$;

In column 3, line 28, delete "$[Cu(amine.BH_2CO_2).H_2O]_2$" and insert --$[Cu(amine.BH_2CO_2)_2.H_2O]_2$--;

In Column 3, line 58, delete "Catternick" and insert --Catterick--;

In column 4, line 5, delete "chemica" and insert --Chimica--;

In column 4, line 23, delete "complex" and insert --complexes--;

In column 4, line 26, delete "97 508-513" and insert --97, 508-513--;

In column 4, line 38, delete "$COO)_2$" and insert --$CO_2)_2$--;

In column 4, line 61, delete "analine" and insert --aniline--;

UNITED STATES PATENT AND TRADEMARK OFFICE
CERTIFICATE OF CORRECTION

PATENT NO. : 4,550,186

DATED : OCTOBER 29, 1985

INVENTOR(S) : ANDREW T. McPHAIL, BERNARD F. SPIELVOGEL, IRIS H. HALL

It is certified that error appears in the above-identified patent and that said Letters Patent is hereby corrected as shown below:

In column 5, line 3, delete "tertiaryamine" and insert --tertiary amine--;

In column 5, line 16, delete "second" and insert --secondary--;

In column 7, line 4, delete "." between N and B

In column 8, line 2, delete "18 104" and insert --18,104--;

In column 8, line 3, delete "42 3175" and insert --42,3175--;

In column 8, line 3, delete "Steward" and insert "Stewart";

In column 8, line 27, delete "$N \cdot BH_2COO]_2 \cdot (CH_3)_3N \cdot BH_2$" and insert --$NBH_2CO_2]_2(CH_3)_3NBH_2$--;

In column 8, line 46, delete "$[Cu(CH_3COO)_2 \cdot CH_3COOH]_2$" and insert --$[Cu(CH_3COO)_2CH_3COOH]_2$--;

UNITED STATES PATENT AND TRADEMARK OFFICE
CERTIFICATE OF CORRECTION

PATENT NO. : 4,550,186
DATED : OCTOBER 29, 1985
INVENTOR(S) : ANDREW T. McPHAIL, BERNARD F. SPIELVOGEL, IRIS H. HALL

It is certified that error appears in the above-identified patent and that said Letters Patent is hereby corrected as shown below:

In column 8, line 50, delete "$[Cu(CH_3COO)_2 \cdot CH_3COOH]_2$" and insert --$[Cu(CH_3COO)_2 CH_3COOH]_2$--;

In column 9, line 11, delete "coordinates listed in Table 1" and insert --reference atom--;

In column 9, line 11, delete "$(-\underline{x},-y,-z)$" and insert --$(\underline{x},\underline{y},\underline{z})$--;

In column 9, line 13, delete "1.49(9)" and insert --1.490(9)--;

In column 9, line 13, delete "1.45(10" and insert --1.495(10--;

In column 9, line 24, delete "coordinates listed in Table I" and insert --reference atom--;

In column 10, line 35, delete "Artherosclerosis" and insert --Atherosclerosis--;

UNITED STATES PATENT AND TRADEMARK OFFICE
CERTIFICATE OF CORRECTION

PATENT NO. : 4,550,186

DATED : OCTOBER 29, 1985

INVENTOR(S) : ANDREW T. McPHAIL, BERNARD F. SPIELVOGEL, IRIS H. HALL

It is certified that error appears in the above-identified patent and that said Letters Patent is hereby corrected as shown below:

In column 10, line 46, delete "[Wade et al, J. Biochem. (Tokyo), 65 71 (1969)]. The digitonide derivative of cholesterol was isolated and counted." and insert --The digitonide derivative of cholesterol was isolated and counted. [Wade et al, J. Biochem. (Tokyo), 65,71 (1969)].--;

In column 10, line 60, delete "-3phosphate" and insert --3-phosphate--;

In column 11, line 52, delete "sectined" and insert --sectioned--;

In column 13, in Table IV, delete "10" and insert --10.0--;

In column 13, in Table III, delete "copper complex (II)" and insert --Copper (II) Complex--;

In column 13, in Table III, delete "synthetase" and insert --Synthetase--;

In column 13, in Table III, delete "$Co_2$" and insert --$CO_2$--;

UNITED STATES PATENT AND TRADEMARK OFFICE
CERTIFICATE OF CORRECTION

PATENT NO. : 4,550,186

DATED : OCTOBER 29, 1985

INVENTOR(S) : ANDREW T. McPHAIL, BERNARD F. SPIELVOGEL, IRIS H. HALL

It is certified that error appears in the above-identified patent and that said Letters Patent is hereby corrected as shown below:

In column 14, line 18, delete "Phosphohydrolase" and insert --phosphohydrolase--;

In column 15, in Table V, fn g, delete "wel" and insert --wet--;

In column 15, in Table V, fn bb, delete "µg/ml" and insert --210 µg/ml--;

In column 17, line 45, delete "methyl phenoxy" and insert --methylphenoxy--;

In column 17, line 49, delete "$^3$-phosphate" and insert --3-phosphate--;

In column 18, line 1, delete "copper complex (II)" and insert --copper (II) complex--;

In column 18, line 2, delete "equal" and insert --equally--;

In column 19, line 29, delete "µmole" and insert --µmol--;

UNITED STATES PATENT AND TRADEMARK OFFICE
CERTIFICATE OF CORRECTION

PATENT NO. : 4,550,186

DATED : OCTOBER 29, 1985

INVENTOR(S) : ANDREW T. McPHAIL, BERNARD F. SPIELVOGEL, IRIS H. HALL

It is certified that error appears in the above-identified patent and that said Letters Patent is hereby corrected as shown below:

In column 20, line 31, delete "pyrocateochol" and insert --pyrocatechol--;

In column 20, in Table VII, delete "$Cu[(CH_3)_3NBH_2CO_2]_2 \cdot CH_3H \cdot BH_2COOH_2]$" and insert --$\{Cu[(CH_3)_3NBH_2CO_2]_2 \cdot (CH_3)_3NBH_2COOH\}_2$--;

In column 21, in Table IX, delete "In vivo" and insert --In Vivo--;

In column 21, in Table IX, in title, delete "$[Cu[(CH_3)_3NBH_2CO_2]_2 \cdot (CH_3)_3N \cdot BH_2COOH_2]$" and insert --$\{Cu[(CH_3)_3NBH_2CO_2]_2 \cdot (CH_3)_3NBH_2COOH\}_2$--;

In column 21, line 11, delete "$^3$-H-Leucine" and insert --$^3$H-Leucine--;

In column 21, line 21, delete "Riboncleotide" and insert --Ribonucleotide--;

UNITED STATES PATENT AND TRADEMARK OFFICE
CERTIFICATE OF CORRECTION

PATENT NO. : 4,550,186

DATED : OCTOBER 29, 1985

INVENTOR(S) : ANDREW T. McPHAIL, BERNARD F. SPIELVOGEL, IRIS H. HALL

It is certified that error appears in the above-identified patent and that said Letters Patent is hereby corrected as shown below:

In column 23, line 18, delete "snythesis" and insert --synthesis--;

In column 24, line 39, delete "atmoms" and insert --atoms--;

In column 24, line 46, delete " $Cu(CH_3)_3N \cdot BH_2CO_2]_2(CH_3)_3N \cdot BH_2COH_2$ " and insert --$\{Cu[(CH_3)_3NBH_2CO_2]_2 \cdot (CH_3)_3NBH_2CO_2H\}_2$--.

Signed and Sealed this

Sixth Day of January, 1987

Attest:

DONALD J. QUIGG

Attesting Officer    Commissioner of Patents and Trademarks

UNITED STATES PATENT AND TRADEMARK OFFICE
CERTIFICATE OF CORRECTION

PATENT NO. : 4,550,186
DATED : OCTOBER 29, 1985
INVENTOR(S) : ANDREW T. McPHAIL ET AL

It is certified that error appears in the above-identified patent and that said Letters Patent is hereby corrected as shown below:

In Column 3, line 58, insert --,-- after 36.

In Column 21, line 17, delete "Ribosmoal" and insert --Ribosomal--.

Signed and Sealed this

Tenth Day of March, 1987

Attest:

DONALD J. QUIGG

*Attesting Officer*　　　*Commissioner of Patents and Trademarks*